United States Patent [19]
Wiktor

[11] Patent Number: 5,782,903
[45] Date of Patent: Jul. 21, 1998

[54] INTRAVASCULAR STENT AND METHOD

[75] Inventor: Dominik M. Wiktor, Cranford, N.J.

[73] Assignee: Medtronic, Inc., Minneapolis, Minn.

[21] Appl. No.: 334,832

[22] Filed: Nov. 4, 1994

Related U.S. Application Data

[63] Continuation-in-part of Ser. No. 872,737, Apr. 22, 1992, which is a continuation of Ser. No. 327,286, Mar. 22, 1989, Pat. No. 5,133,732, which is a continuation-in-part of Ser. No. 109,686, Oct. 19, 1987, Pat. No. 4,886,062.

[51] Int. Cl.$^6$ .................................................. A61B 17/00
[52] U.S. Cl. ................................................. 623/1; 606/195
[58] Field of Search ............................. 606/195, 191, 606/192, 194, 198; 623/1, 12

[56] References Cited

U.S. PATENT DOCUMENTS

| | | | |
|---|---|---|---|
| 3,896,814 | 7/1975 | Vivien et al. | 128/335.5 |
| 3,942,532 | 3/1976 | Hunter et al. | 128/335.5 |
| 4,027,676 | 6/1977 | Mattei | 128/335.5 |
| 4,047,533 | 9/1977 | Perciaccante et al. | 128/335.5 |
| 4,105,034 | 8/1978 | Shalaby et al. | 128/335.5 |
| 4,185,637 | 1/1980 | Mattei | 128/335.5 |
| 4,195,637 | 4/1980 | Gruntzig et al. | 128/348 |
| 4,201,216 | 5/1980 | Mattei | 128/335.5 |
| 4,402,307 | 9/1983 | Hanson et al. | 128/1 D |
| 4,531,993 | 7/1985 | Bradley | 156/227 |
| 4,532,929 | 8/1985 | Mattei et al. | 128/335.5 |
| 4,649,920 | 3/1987 | Rhum | 128/335.5 |
| 4,711,241 | 12/1987 | Lehmann | 128/335.5 |
| 4,790,809 | 12/1988 | Kuntz | 604/8 |
| 4,791,929 | 12/1988 | Jarrett et al. | 128/335.5 |
| 4,820,262 | 4/1989 | Finney | 604/8 |
| 4,886,062 | 12/1989 | Wiktor | 128/343 |
| 4,893,623 | 1/1990 | Rosenbluth | 606/192 |
| 4,950,228 | 8/1990 | Knapp, Jr. et al. | 604/8 |
| 4,983,180 | 1/1991 | Kawai et al. | 606/230 |
| 4,990,133 | 2/1991 | Solazzo | 604/8 |
| 4,990,151 | 2/1991 | Wallsten | 606/108 |
| 4,994,066 | 2/1991 | Voss | 606/108 |
| 4,994,074 | 2/1991 | Beswada et al. | 606/230 |
| 5,017,407 | 5/1991 | Robertson | 427/349 |
| 5,019,085 | 5/1991 | Hillstead | 606/108 |
| 5,019,090 | 5/1991 | Pinchuk | 606/194 |
| 5,035,706 | 7/1991 | Giantureo et al. | 606/198 |
| 5,037,427 | 8/1991 | Harada et al. | 606/108 |
| 5,052,998 | 10/1991 | Zimmon | 604/8 |
| 5,071,407 | 12/1991 | Termin et al. | 604/104 |
| 5,089,013 | 2/1992 | Bezwada et al. | 606/228 |
| 5,092,877 | 3/1992 | Pinchuk | 623/1 |
| 5,098,440 | 3/1992 | Hillstead | 606/108 |
| 5,100,433 | 3/1992 | Beswada et al. | 606/230 |
| 5,102,420 | 4/1992 | Hunter et al. | 606/231 |
| 5,123,912 | 6/1992 | Kaplan et al. | 606/230 |
| 5,133,732 | 7/1992 | Wiktor | 606/195 |
| 5,147,383 | 9/1992 | Bezwada et al. | 606/231 |
| 5,167,614 | 12/1992 | Tessman et al. | 604/8 |
| 5,176,626 | 1/1993 | Soehendra | 604/8 |
| 5,222,971 | 6/1993 | Willard et al. | 606/158 |
| 5,226,913 | 7/1993 | Pinchuk | 623/1 |
| 5,269,802 | 12/1993 | Garber | 606/191 |
| 5,290,294 | 3/1994 | Cox et al. | 606/108 |
| 5,304,122 | 4/1994 | Schwartz et al. | 604/53 |
| 5,306,289 | 4/1994 | Kaplan et al. | 606/228 |
| 5,549,624 | 8/1996 | Mirigian et al. | 606/191 |
| 5,582,619 | 12/1996 | Ken | 606/191 |

OTHER PUBLICATIONS

Roland, M., "Spiral Teflon Stent for Tuboplasty Involving Fimbria", Obstetrics and Gynecolgy vol. 6, No. 3, 359–62, Sep. 1970.

*Primary Examiner*—Michael Buiz
*Assistant Examiner*—Kevin Truong
*Attorney, Agent, or Firm*—Daniel W. Latham; Harold R. Patton

[57] ABSTRACT

A stent for providing support to a body lumen comprises a wire wound in a continuous winding into a generally cylindrical shape with the cylindrical shape terminating at one end in a closed loop of the wire and a line of elongated flexible material extending through the closed loop and looped back on itself at the closed loop such that the line is secured to the winding at the closed loop and is freely slideable through the closed loop. If necessary, this stent can be readily removed from the body lumen after implantation or left in the body lumen as a permanent implant.

37 Claims, 2 Drawing Sheets

INTRAVASCULAR STENT AND METHOD

CROSS REFERENCE TO RELATED APPLICATIONS

This is a continuation-in-part of U.S. patent application Ser. No. 872,737, filed Apr. 22, 1992, which is a continuation of U.S patent application Ser. No. 327,286, filed Mar. 22, 1989, now U.S. Pat. No. 5,133,732, which is a continuation-in-part of U.S. patent application Ser. No. 109,686, filed Oct. 19, 1987, now U.S. Pat. No. 4,886,062.

FIELD OF THE INVENTION

This invention relates to intravascular implants for maintaining vascular patency in humans and animals. The present invention comprises an open-ended wire formed device of basically cylindrical shape and made of a softer-than spring type metal and fitted over an inflatable element of a typical balloon type catheter such as described in U.S. Pat. No. 4,195,637 and U.S. Pat. No. 4,402,307. The wire formed device is intended to act as either a permanent or removable prosthesis stent and is implanted and optionally removed transluminarely. Specifically, this invention is characterized by the ability of said intravascular stent to be enlarged radially after having been introduced percutaneously, transported transluminarely and positioned at a desired location. In addition, this invention relates to a method whereby a permanent (or temporary) prosthesis stent is implanted at the same time as the angioplasty procedure is being performed. Further, this invention relates to a device which can be readily removed following its implantation or left as a permanent implant. This invention is particularly useful in transluminar implantation of a stent in the field of cardiology and especially in the case of coronary angioplasty to prevent restenosis.

BACKGROUND OF THE INVENTION

In my U.S. Pat. No. 4,886,062, which is hereby incorporated herein by reference in its entirety, a wire formed device is described as shown in FIG. 1 in which a wire 2 is initially preformed into a two-dimensional zig-zag form 3, basically creating a flat, expandable shape. This can be conveniently accomplished by the conventional expedients of either hand-forming the wire or running the wire through intermeshed gear teeth of a size and orientation to provide a desired zig-zag form. The zig-zag pattern can vary as to its shape and tightness of the reversing bends, but for reasons of simple description a typical sinusoidal form is chosen to depict this zig-zag construction. A length of the zig-zag form 3 is wrapped on a suitable mandrel 4 in a manner similar to that of winding a simple helical spring. Care is taken to form the wire form 3 flat against the mandrel 4 with little or no tension to prevent premature linear expansion of form 3. Once the zig-zag form 3 is wound into a cylindrical shape, it is removed from the mandrel 4, and is placed over a suitable variable diameter device such as an inflatable balloon 5 typically used for angioplasty procedures as shown in FIG. 2. A suitable forming tool (not shown) is used to tighten the stent over the balloon; manual operation of squeezing the over the balloon is also acceptable. A controlled radial expansion of the stent is accomplished by the force generated by the inflating balloon. When acted upon by the inflating balloon, the stent, being characterized by the zig-zag preformed wire form 3 formed into a cylindrical shape, is by design and intent capable of expanding radially. The radial expansion in effect is achieved by controlled deformation and tension applied to the sinusoidal pattern of the preformed wire form 3. The low memory metal used for the fabrication of the wire formed stent assures that the radially expanded stent stays expanded, thus fulfilling its primary intent and function as a stent in a body vessel.

In angioplasty procedures, in many cases restenosis occurs soon thereafter, which requires a secondary procedure or a surgical bypass operation. The implanted stent, as described above, will provide mechanical support for the vessel and thereby maintain its patency. Depending on the size used, the stent described above can also be efficacious in other similar applications, such as: repairs of aneurysms, support of artificial vessels or liners of vessels, initial repairs of dissections and mechanical support to prevent collapsing of dilated vessels. A possible disadvantage of the device disclosed in my U.S. Pat. No. 4,886,062 is that it does not necessarily lend itself to easy removal if it is decided that the device is mispositioned in the vessel or if it is to be only inserted for a brief period of time and then removed.

Methods intended to address this problem include the conventional expedient of employing a snaring tool as disclosed in U.S. Pat. No. 5,019,090 issued to Pinchuk or U.S. Pat. No. 5,098,440 issued to Hillstead. However, such devices can cause damage to the vessel at a site which may already have sustained some injury due to balloon expansion or stent placement. Another approach to the problem is to provide an extended wire tail on the stent which can be used to pull the stent out of the vessel. Such stents have been disclosed in U.S. Pat. No. 5,017,407 issued to Termin or in an earlier disclosure in Roland, M., *Spiral Teflon Stent for Tuboplasty Involving Fimbria*, Obstetrics and Gynecology, Vol. 36, No. 3, September 1970. This approach is suitable for stents which are only to be implanted temporarily since the extended tail would be undesirable in a permanent implant.

It is therefore an object of the present invention to provide a stent which may be readily removed with minimal opportunity for damage to the blood vessel.

It is also an object of the present invention to provide a stent which may be optionally used as a temporary or permanent implant.

It is also an object of the present invention to provide a method for implanting an removing a stent with minimal opportunity for damage to the blood vessel.

SUMMARY OF THE INVENTION

These and other objects are accomplished by the stent and method of the present invention. I have discovered a stent for providing support to a body lumen which includes a wire wound in a continuous winding into a generally cylindrical shape in which the cylindrical shape terminates at one end in a closed loop of the wire. A line of elongated flexible material extends through the closed loop and looped back on itself at the closed loop such that the line is secured to the winding at the closed loop and is freely slideable through the closed loop. In its most basic mode of operation, the stent is implanted transluminally in a desired location in a blood vessel with the two legs of the line trailing in a proximal direction from the stent through the incision in the blood vessel. If the physician determines that the stent is mispositioned in the blood vessel, it can be removed by pulling on the legs of the line, which causes the line to be withdrawn and the winding to be uncoiled and removed from the lumen in an opened condition. If the physician determines that the stent is properly positioned, the line can be removed by releasing one leg of the line and pulling the other leg until the line is pulled through the closed loop and removed from the blood vessel.

A number of preferred embodiments also relate to the general concept of the stent as described above. A particularly preferred embodiment of the invention is to make the winding portion of the stent a helical winding as disclosed in my U.S. Pat. No. 4,886,062 which is a helically wound device which may be readily removed by unwinding. The closed loop can also be the closed loop substantially as disclosed in that same patent or it can be provided by attaching an end of the wire of the winding to an adjacent turn of the helix. Since the stent is most conveniently removed from its proximal end, the closed loop is preferably at the proximal end of the stent winding. As for the line, the ends of the line can be secured together at a point remote from the closed loop in order to prevent the line from inadvertently slipping through the loop. If the stent is to be left in place, the line can then be severed and drawn back through the closed loop by releasing one leg of the line and drawing it through the closed loop by pulling on the other leg.

Since it is critical in the present invention that the line be able to slide through closed loop, improvements may be made to the line to improve its pliability and ability to slide with respect to the loop. Line materials which can be used in the present invention include surgical suture materials having suitable slip and pliability properties. Sutures have been constructed from a wide variety of materials including surgical gut, silk, cotton, a polyolefin such as polypropylene, polyamide, polyglycolic acid, polyesters such as polyethylene terephthalate and glycolide-lactide copolymer, etc. Since some materials of construction will result in a stiff monofilament that is unsuitable in the present invention, sutures manufactured from such materials are preferably provided as multifilament braided structures. Such multifilament suture material typically requires a surface coating to improve the pliability and slip characteristics of the suture. For example, known coating materials for sutures include silicones, waxes, polytetrafluoroethylene (PTFE) and many other polymers. Numerous patents disclose such coated sutures including, U.S. Pat. Nos. 5,306,289; 5,147,383; 5,123,912; 5,102,420; 5,100,433; 5,089,013; 4,994,074; 4,983,180; 4,791,929; 4,711,241; 4,649,920; 4,532,929; 4,201,216; 4,185,637; 4,105,034; 4,047,533; 4,027,676; 3,942,532 and 3,896,814 which are incorporated herein by reference. The suture material used can be either a biostable or a bioabsorbable material. The loop can also be provided with coatings which promote the slip of the line through the loop. For example, polyfluorotetraethylene (PTFE) or ultra-high molecular weight polyethylene could be coated onto the closed loop.

The present invention also preferably includes a catheter into which the wire winding is drawn. For example, if it is determined that the stent should be removed, a catheter having a lumen can be threaded over the line and guided to the stent site. Since the line is made from a highly flexible material, threading the line through the catheter lumen can be facilitated by use of an element with greater stiffness such as a guidewire or guidewire extension attached to the line. The line then emerges from the catheter at the proximal end where it may be used to draw the wire winding of the stent into the catheter and then withdrawing the catheter and the stent. The stent can then be withdrawn completely through the catheter lumen or the catheter and stent can be withdrawn as a unit. This method of stent removal provides improved protection from injury to the vessel wall as the stent is withdrawn. Alternatively, the catheter can be the same catheter used to implant the stent, such as a balloon catheter, which includes a lumen into which the stent can be pulled if the implantation is unsuccessful. In such a catheter, the catheter could be introduced with the wire winding of the stent at a distal end and with the line extending through a lumen of the catheter and emerging from the catheter at a proximal end. Once the stent is deployed by expansion of the balloon, the balloon can be deflated to allow blood to flow through the stented lumen. The stent so implanted can be used as a temporary support for a desired period of time and then removed by pulling the wire winding of the stent into the catheter and removing the catheter. If the stent and catheter were to be used only for temporary support, the line could be secured to the catheter at one leg such that the free leg of the line could be pulled to remove the wire winding. If permanent implantation were desired, the catheter could also include a remote release to release the secured leg of the line if the stent were successfully implanted.

DETAILED DESCRIPTION OF THE INVENTION

The stent of the present invention is a radially expandable stent for implantation within a body lumen having a continuous wire winding defining a generally cylindrical shape. A stent having a winding of this type is described, for example, in my U.S. Pat. No. 4,886,062. The winding has a closed loop at one end and an elongated line extends through the loop, thereby attaching it to the proximal end of the stent winding with the legs of the line extending away therefrom in a proximal direction and means at a proximal end of the line remote from the winding for retracting the line and thereby uncoiling the winding to facilitate its removal in an opened condition.

Figure 1:
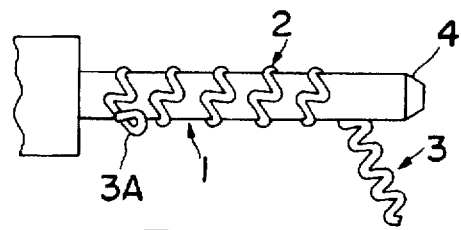
FIG. 1 is a side elevation of a preferred embodiment of a stent according to this invention being wound on a mandrel.

Therefore, the configuration to which this invention in particularly directed is shown in FIG. 1. A wire 2 (having a preferred diameter in the range of about 0.005 inch to 0.010 inch) is initially preformed into a two-dimensional zig-zag form 3. The zig-zag pattern can vary as to its shape and the tightness of the reversing bends, but for reasons of simple description a typical sinusoidal form is chosen to depict the band's construction.

Figure 2:
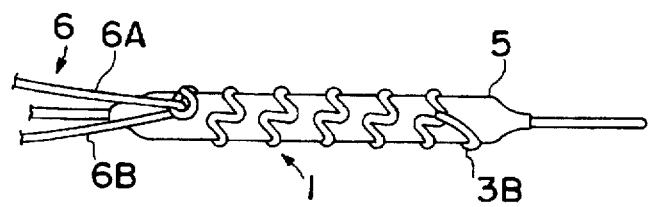
FIG. 2 is a side elevation showing an overall view of a stent prosthesis according to this invention fitted over a deflated balloon.
Figure 5:
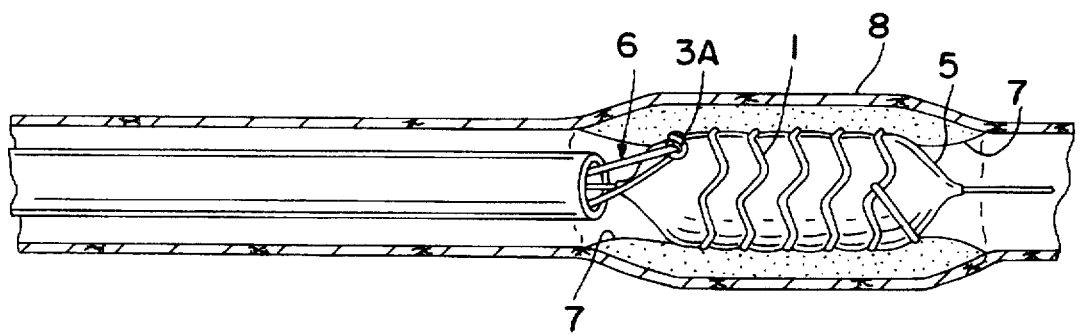
FIG. 5 is similar to FIG. 4 showing the balloon being inflated and the stent being radially expanded, illustrating an angioplasty procedure coupled with a simultaneous deployment and implantation of a prosthesis stent.

In order to create coiled winding 1, and to have it assume an initial configuration as shown at 1 in FIG. 1, and also the subsequently radially expanded condition as shown in FIG. 5, a length of the two-dimensional zig-zag form 3 is wrapped or coiled on a suitable mandrel 4 in a manner similar to that of winding a simple helical spring. Again this is as shown in FIG. 1 and provides the coiled winding 1. Care is taken to form the wire form 3 flat around the mandrel with little or no tension to prevent premature linear expansion of wire form 3. The wire form 3 is shown terminated at a proximal end by a closed loop 3A and at a distal end by securing the end loop 3B to the last coil of the winding as shown in FIG. 2. Since either of these methods of termination form a closed loop, either form may be used as the closed loop for the purposes of the present invention. Since the closed loop 3A is to be used for pulling on the winding, it will be apparent to those skilled in the art that the loop 3A must be securely closed (for example, by welding closed) to resist pulling forces.

Once the zig-zag wire form 3 is wound into a coiled winding 1, it is removed from the mandrel 4, and is placed over a suitable expandable diameter device such as an inflatable balloon 5 typically used for angioplasty procedures. This is shown in FIG. 2. A suitable crimping tool (not shown) may be used to tighten the winding over the balloon. Manual operation of squeezing the winding over the balloon is also acceptable. A line 6 of flexible, elongated material, is threaded through the closed loop 3A such that the line 6 is secured to the winding 1 such that first and second legs 6A, 6B extend away from the winding in a proximal direction. The legs 6A, 6B may be of various lengths. They may extend the entire length of a catheter in which case a length of four or five feet may be used or even longer lengths where certain catheter exchange procedures are to be used. It may also be only a few inches long in order to provide a ready connection to another element which can effect the uncoiling of the stent winding.

Controlled radial expansion of the stent winding is accomplished by the force generated in inflating the balloon. When acted upon by the inflating balloon the stent winding, being characterized by the zig-zag preformed wire form 3, is subsequently formed into an open-ended cylindrical shape. By design and intent it is capable of expanding radially.

The radial expansion in effect is achieved by controlled deformation and tension applied to the sinusoidal pattern of the preformed wire form 3. The low memory metal used for the fabrication of the wire formed stent winding assures that the radially expanded stent winding stays expanded thus fulfilling its primary intent and function to provide support in a body lumen such as a blood vessel for any flaps or dissections in the lumen wall.

For purposes of better understanding this invention detailed reference is made to FIGS. 1–6. The preferred embodiment of this invention is shown and described in an application for angioplasty; however, it is understood that other applications not specifically mentioned herein are possible and no limitations in scope of this invention are intended or implied.

The wire used for the stent winding may be made of drawn low-memory level material such as tantalum, stainless steel, titanium ASTM F63-83 Grade 1 or high carat gold K 19–22. Copper alloy typically 110 when properly coated with polyester or Teflon can also be used. Titanium and gold are biologically compatible and inert and require no special treatment. Tantalum is the preferred stent winding material.

Figure 6:
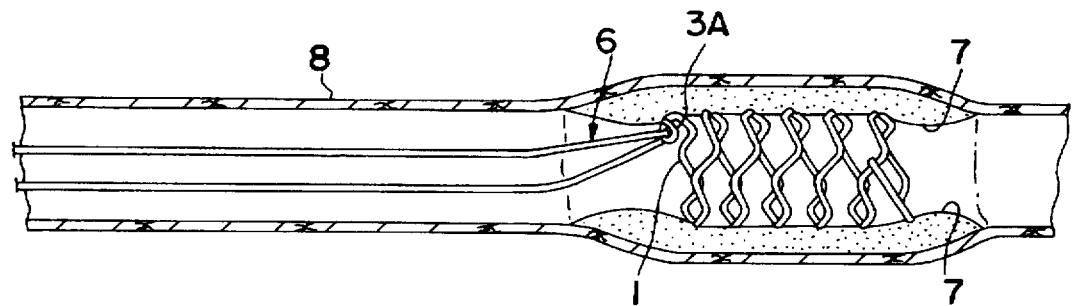
FIG. 6 is a view similar to FIG. 5 showing the prosthesis stent implanted and plaque compressed and retained after removal of the balloon.

In FIG. 2 it is seen that winding 1 is centrally located and positioned with respect to the length of balloon 5 and that zig-zag wire form 3 turns are evenly spaced so that when winding 1 is expanded as shown in FIG. 5 and FIG. 6, the winding 1 will provide even support inside vessel 8 and be able to resist external loading. The legs 6A, 6B of elongated line 6 are merely left to extend proximally from the end of the winding 1.

Figure 3:
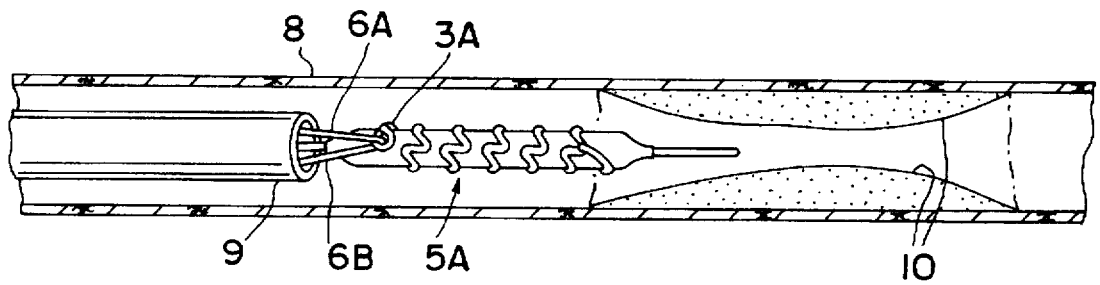
FIG. 3 shows the balloon and stent assembly of FIG. 2 advanced within a vessel, approaching a partial occlusion.
Figure 4:
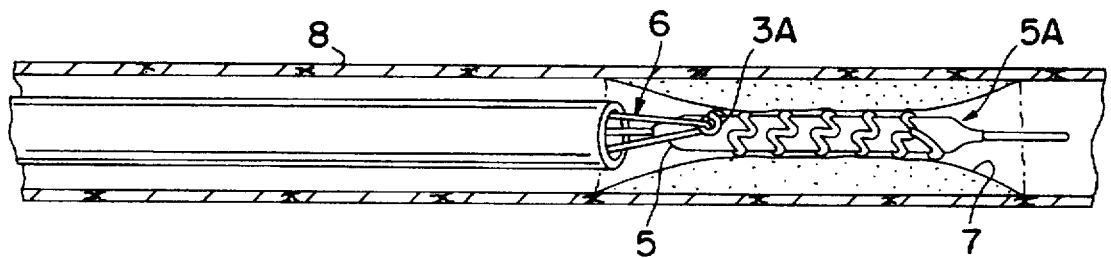
FIG. 4 is similar to FIG. 3 showing the balloon and stent assembly inside a partially occluded vessel.

In FIG. 3 it is seen how balloon and stent assembly 5A, including legs 6A, 6B of line 6, emanate from guiding catheter 9 inside vessel 8 and are advanced towards partial occlusion 10. It will be appreciated by those skilled in the art that although the balloon and stent assembly 5A is shown with an undilated occlusion 10, the stent of the present invention can also be used in pre-dilated vessels in order to support flaps or dissections caused by the dilation procedure. It will also be appreciated that a conventional guidewire may be employed to assist deployment of the assembly 5A into the occlusion 10. In FIG. 4 it is seen how balloon and stent assembly 5A are located in occlusion 10 within artery 8, balloon 5 still being deflated. Once positively placed, such as within occlusion 10, balloon 5 is inflated using standard angioplasty procedures and techniques. As balloon 5 expands, so does winding 1 as shown in FIG. 5. The expanding balloon 5 together with winding 1 contacts the plaque 7 and expands the vessel 8. With the angioplasty procedure completed, balloon 5 is deflated and withdrawn leaving winding 1 firmly implanted within vessel 8. Previously occluded vessel 8 is now supported by winding 1 and patency is restored. Again, elongated line 6 is raerely left in place, the legs 6A, 6B of which are extending in a proximal direction from the closed loop 3A of the stent winding. The guiding catheter 9 is also shown to have been withdrawn although it may also be left in place in order to facilitate removal of the stent winding.

FIG. 6 shows winding 1 firmly implanted and imbedded in plaque 7 providing both adequate support as well as a vessel 8 without protrusions, flaps and dissections to obstruct blood flow. The winding 1 may then remain in place for the period of time required for any flaps or dissections caused by the dilation of the balloon 5 to re-adhere to the wall of the vessel 8. Since the angioplasty balloon is deflated during this period, blood flow through the lumen is not constricted even though the balloon catheter may remain positioned in the body lumen at the site of the angioplasty. When removal is desired, grasping the legs 6A and 6B of the line 6 and gently pulling on them simultaneously results in the uncoiling of the stent. If the guiding catheter has remained in place, the line 6 can be pulled until the line and stent are completely removed from the guiding catheter 9. The result is removal of a long piece of relatively straight wire. If desired, the stent can be pulled out at the same time as the balloon angioplasty catheter, before the balloon angioplasty catheter is removed or after the balloon angioplasty catheter is removed. The stent can also be removed at the same time as the removal of the guiding catheter or before or after removal of the guiding catheter although most physicians would find it preferable to leave the guiding catheter in place until the stent is removed.

This improvement in the stent design greatly accommodates retrievability. The sinusoid waves or zig zag form in the stent wire straighten during the retrieval procedure and the procedure is completed with minimal trauma to the vessel wall.

Alternatively, the stent winding 1 can be left in place as a permanent implant by removing line 6. This can be accomplished by releasing leg 6B and pulling on leg 6A until the line 6 is pulled through closed loop 3A.

In a preferred embodiment, the invention also includes a catheter device for removing a stent having a continuous winding from a body lumen with minimum trauma to the blood vessels. This device is typically employed after the balloon catheter and guidewire have been removed. The device comprises a catheter with a short lumen at a distal end of the catheter which is designed to receive a line attached to a closed loop at a proximal end of the stent winding. The line is threaded into the short lumen and the catheter is advanced over the line until it is in proximity to the stent winding. The line then extends through the short lumen and follows along the exterior of the catheter until it emerges from the body where it can be pulled to uncoil the stent winding. By pulling on the line, the zig zag form of the stent winding uncoils and contacts the distal edge of the catheter tube. The stent winding is then drawn into the short lumen causing it to be further straightened. The catheter and stent are then withdrawn with the straightened stent held in the short lumen of the catheter. Keeping the stent confined inside the short lumen as it is withdrawn eliminates the trauma of the stent rubbing against the vessel walls as it is withdrawn. In this embodiment, therefore, the short lumen only needs to be long enough to accommodate the length of the uncoiled stent.

This completes the description of the preferred and alternate embodiments of the invention. Those skilled in the art may recognize other equivalents to the specific embodiment described herein which equivalents are intended to be encompassed by the claims attached hereto.

I claim:

1. A stent for providing support to a body lumen comprising:
   (a) a wire wound in a continuous winding into a generally cylindrical shape, the cylindrical shape terminating at one end in a closed loop of the wire; and
   (b) a line of elongated flexible material, the line extending through the closed loop and looped back on itself at the closed loop such that the line is secured to the winding at the closed loop and is freely slideable through the closed loop.

2. The stent of claim 1 wherein the continuous winding has a generally helical configuration.

3. The stent of claim 2 wherein the closed loop is provided by attaching an end of the wire to an adjacent turn of the helix.

4. The stent of claim 1 wherein the closed loop is provided at a proximal end of the winding.

5. The stent of claim 1 wherein the closed loop includes means for improving the slideability of the line through the closed loop.

6. The stent of claim 1 wherein the line includes means for improving the slideability of the line through the closed loop.

7. The stent of claim 1 wherein the line has a first end and a second end secured together at a point remote from the closed loop.

8. The stent of claim 1 wherein the flexible line material is a biostable polymeric material.

9. The stent of claim 1 wherein the flexible line material is a bioabsorbable polymeric material.

10. A device for providing support to a body lumen comprising:
    (a) a wire wound in a continuous winding into a generally cylindrical shape, the cylindrical shape terminating at one end in a closed loop of the wire;
    (b) a line of elongated flexible material, the line extending through the closed loop and looped back on itself at the closed loop such that the line is secured to the winding at the closed loop and is freely slideable through the closed loop; and
    (c) a catheter having a lumen extending from a distal end of the catheter, said line of elongated, flexible material extending through the catheter lumen, said line entering at distal end of the lumen and emerging at a proximal end of the lumen.

11. The device of claim 10 wherein the continuous winding has a generally helical configuration.

12. The device of claim 11 wherein the closed loop is provided by attaching an end of the wire to an adjacent turn of the helix.

13. The device of claim 10 wherein the closed loop is provided at a proximal end of the winding.

14. The device of claim 10 wherein the closed loop includes means for improving the slideability of the line through the closed loop.

15. The device of claim 10 wherein the line includes means for improving the slideability of the line through the closed loop and through the catheter.

16. The device of claim 10 wherein the line has a first end and a second end secured together at a point remote from the closed loop.

17. The device of claim 10 wherein the flexible line material is a biostable polymeric material.

18. The device of claim 10 wherein the flexible line material is a bioabsorbable polymeric material.

19. The device of claim 10 wherein the catheter also includes means for securing the line to the catheter and means for remotely releasing the secured line from the catheter.

20. A device for providing support to a body lumen comprising:
    (a) a catheter having a lumen extending from a distal end to a proximal end of the catheter and a balloon at the distal end;
    (b) a wire wound in a continuous winding into a generally cylindrical shape around the balloon, the cylindrical shape terminating at one end in a closed loop of the wire; and
    (c) a line of elongated flexible material, the line extending through the closed loop and looped back on itself at the closed loop such that the line is secured to the winding at the closed loop and is freely slideable though the closed loop and such that the line extends through the lumen of the catheter from the distal end to the proximal end.

21. The device of claim 20 wherein the line includes means for improving the slideability of the line through the closed loop and through the catheter.

22. The device of claim 20 wherein the line has a first end and a second end secured together at a point remote from the closed loop.

23. The device of claim 20 wherein the catheter also includes means for securing the line to the catheter and means for remotely releasing the secured line from the catheter.

24. A method for temporary implantation of a stent in a body lumen comprising:
    (a) providing a catheter;
    (b) providing a continuous winding mounted on the catheter in a generally cylindrical shape terminating at one end in a closed loop;
    (c) providing a line of elongated flexible material extending through the closed loop and looped back on itself at the closed loop such that the line is secured to the winding at the closed loop and is freely slideable through the closed loop;
    (d) placing the catheter, continuous winding and line into the body lumen with the continuous winding positioned at the portion of the body lumen to be supported;

(e) expanding the positioned continuous winding into supporting contact with the body lumen and releasing the winding from the catheter;

(f) maintaining the support of the body vessel with the expanded continuous winding for a desired period of time; and (g) withdrawing the line at the expiration of the desired period of time at a point remote from the winding such that the winding is uncoiled and removed from the lumen in an opened condition.

25. The method of claim 24 wherein the line looped back on itself forms first and second legs extending in a proximal direction from the winding.

26. The method of claim 25 wherein the line is withdrawn by moving the first and second legs simultaneously.

27. The method of claim 25 wherein the line is withdrawn by moving the first leg and keeping the second leg in a fixed position.

28. The method of claim 24 wherein the line is withdrawn through a lumen of the catheter.

29. The method of claim 28 wherein the winding is withdrawn through the catheter lumen.

30. A method for implantation of a stent in a body lumen comprising:

(a) providing a catheter;

(b) providing a continuous winding on the catheter in a generally cylindrical shape terminating at one end in a closed loop;

(c) providing a line of elongated flexible material extending through the closed loop and looped back on itself at the closed loop such that the line is secured to the winding at the closed loop and is freely slideable through the closed loop;

(d) placing the catheter, continuous winding and line into the body lumen with the continuous winding positioned at the portion of the body lumen to be supported;

(e) expanding the positioned continuous winding into supporting contact with the body lumen;

(f) withdrawing the line at a point remote from the winding such that the line is removed from the closed loop of the expanded winding and the winding remains in supporting contact with the body lumen.

31. The method of claim 30 wherein the line looped back on itself forms first and second legs extending in a proximal direction from the winding.

32. The method of claim 31 wherein the line is withdrawn by severing the first leg and withdrawing the second leg.

33. The method of claim 30 wherein the line is withdrawn through a lumen of the catheter.

34. The method of claim 33 wherein the winding is withdrawn through the catheter lumen.

35. A method for removing a stent implanted in a body lumen comprising:

(a) providing a continuous winding in supporting contact with the body lumen, said continuous winding in a generally cylindrical shape terminating at one end in a closed loop;

(b) providing a line of elongated flexible material extending through the closed loop and looped back on itself at the closed loop such that the line is secured to the winding at the closed loop and is freely slideable through the closed loop;

(c) providing a catheter having a lumen at a distal end thereof;

(d) placing the line through the lumen of the catheter and advancing the catheter into the body lumen to a desired position in proximity with the stent; and (e) withdrawing the line at a point remote from the continuous winding to effect the uncoiling of the winding and removal of the winding into the catheter lumen in an opened condition.

36. The method of claim 35 wherein the line looped back on itself forms first and second legs extending in a proximal direction from the winding.

37. The method of claim 36 wherein the line is withdrawn by severing the first leg and withdrawing the second leg.

\* \* \* \* \*